(12) United States Patent
Dupont et al.

(10) Patent No.: US 6,583,095 B1
(45) Date of Patent: *Jun. 24, 2003

(54) SYNTHESIS OF BLEACH ACTIVATORS

(75) Inventors: Jeffrey Scott Dupont, Cincinnati, OH (US); Robert Richard Dykstra, Cleves, OH (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/831,197

(22) PCT Filed: Nov. 19, 1999

(86) PCT No.: PCT/US99/27501

§ 371 (c)(1),
(2), (4) Date: May 7, 2001

(87) PCT Pub. No.: WO00/31028

PCT Pub. Date: Jun. 2, 2000

Related U.S. Application Data

(60) Provisional application No. 60/109,152, filed on Nov. 20, 1998.

(51) Int. Cl.[7] .............................. C11D 7/26; C11D 7/32; C11D 7/54
(52) U.S. Cl. ...................... 510/313; 510/376; 510/501; 554/68; 554/70; 252/186.38
(58) Field of Search ................................. 510/312, 313, 510/376, 501; 554/68, 70; 252/186.38

(56) References Cited

U.S. PATENT DOCUMENTS

| | | | |
|---|---|---|---|
| 5,153,541 A | 10/1992 | Johnson et al. | |
| 5,286,879 A | 2/1994 | Letton et al. | |
| 5,391,780 A | 2/1995 | Zima et al. | |
| 5,393,901 A | 2/1995 | Zima et al. | |
| 5,393,905 A | 2/1995 | Zima et al. | |
| 5,414,099 A | 5/1995 | Heinzman et al. | |
| 5,466,840 A | 11/1995 | Lutz et al. | |
| 5,523,434 A | 6/1996 | Burns et al. | |
| 5,534,642 A | 7/1996 | Heinzman et al. | |
| 5,576,282 A | 11/1996 | Miracle et al. | |
| 5,650,527 A | 7/1997 | Lutz et al. | |
| 5,710,116 A | 1/1998 | Miracle et al. | |
| 5,817,614 A | 10/1998 | Miracle et al. | |
| 6,369,250 B1 * | 4/2002 | Dykstra et al. | ................ 554/70 |

FOREIGN PATENT DOCUMENTS

| | | | |
|---|---|---|---|
| WO | WO 95/26397 A1 | 10/1995 | |
| WO | WO 96/23873 A1 | 8/1996 | |
| WO | WO 99/09004 | * | 2/1999 |

* cited by examiner

*Primary Examiner*—Gregory Delcotto
(74) *Attorney, Agent, or Firm*—James F. McBride; Kim W. Zerby; Steve W. Miler

(57) ABSTRACT

The present invention relates to an improved process for synthesizing organic compounds for use as bleach activators.

9 Claims, No Drawings

SYNTHESIS OF BLEACH ACTIVATORS

CROSS REFERENCE TO RELATED APPLICATIONS

This application is an entry into the U.S. National Stage under 35 U.S.C. §371 of PCT International Application Serial No. PCT/US99/27501, filed Nov. 19, 1999, which claims priority under PCT Article 8 and 35 U.S.C. §119(e) to U.S. Provisional Application Serial No. 60/109,152, filed Nov. 20, 1998, (now abandoned).

FIELD OF THE INVENTION

The present invention relates to an improved process for synthesizing organic compounds for use as bleach activators.

BACKGROUND OF THE INVENTION

The synthesis of ingredients for use in low unit cost consumer goods such as laundry detergents, fabric softeners, and the like is of considerable interest to manufacturers. Indeed, the low cost synthesis of ingredients is typically the rate limiting step in the course of bringing a consumer product to the market. Due to the large number of ingredients in consumer goods such as laundry detergents, the expense of individual ingredients must be minimized in order to keep the cumulative product cost within acceptable ranges. The expense associated with the manufacture of consumer goods ingredients is often due to either the cost of the raw materials used to make such ingredients or to the complex reaction and processing chemistry which is required in their manufacture. Accordingly, manufacturers conduct a continuing search for both inexpensive raw materials or simplified reaction sequences.

Amido acid phenyl ester sulfonates form a class of materials which can serve as bleach activators in laundry detergents and other types of bleach-containing cleaning compositions. Such activators have several desirable attributes including excellent bleaching performance with minimal color damage on fabrics dyes, good washing machine compatibility and a good odor profile in the wash. While these materials are potentially obtainable from inexpensive raw materials, the synthesis is somewhat complicated and typically involves the use of solvents. Problems can also arise in the formation of color impurities, caused by the reaction of color forming bodies, in the end product. These color forming impurities or bodies result in a finished product which is undesirable to consumers and consequently unusable because of its appearance. This results in additional steps to remove the colored impurities. These additional steps have the problem that not only do they remove the colored impurities, add additional time and cost, but they also remove some of the amido acid phenyl ester sulfonates along with the colored impurities. Thus, the synthesis of amido acid phenyl ester sulfonates is not straightforward and can be surprisingly problematic.

Accordingly, the need remains for a simple, inexpensive yet effective process for the production of amido acid phenyl ester sulfonates which does not result in the formation of colored impurities in the final product.

BACKGROUND ART

U.S. Pat. Nos. 5,466,840, 5,391,780, 5,393,901, 5,393, 905, 5,523,434, 5,391,780, 5,414,099, 5,534,642, 5,153,541, 5,650,527, 5,286,879 and 5,523,434.

SUMMARY OF THE INVENTION

This need is met by the present invention, wherein improved process for preparing a purified amido acid phenyl ester sulfonate are provided.

According to a first aspect of the present invention, a process for the preparation a 4-sulfophenyl-[(1-oxyalkanoyl)amino]alkanoate is provided. The process comprises the steps of:

reacting an acetoxy benzene sulfonate salt with a high purity amido carboxylic acid, wherein said high purity amido carboxylic acid comprises least about 90%, preferably about 95%, even more preferably about 97% by weight, of a amido carboxylic acid of the formula:

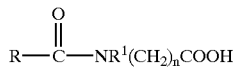

wherein R is $C_5$–$C_{21}$ hydrocarbyl, $R^1$ is selected from hydrogen and $C_1$–$C_3$ alkyl, and n is an integer from about 1 to about 8; and less than about 10% by weight, of color forming bodies;

wherein the process is performed in the presence of less than about 10 ppm, preferably less than about 5 ppm, more preferably less than about 2 ppm, even more preferably less than about 0.5 ppm of transition metals, preferably selected from the group consisting of iron, nickel, chromium and mixtures thereof, more preferably iron, nickel, and mixtures thereof According to a second aspect of the present invention, the process for preparing a 4-sulfophenyl-[(1-oxyalkanoyl) amino]alkanoate comprising the steps of:

(a) reacting a high purity amido carboxylic acid, wherein said high purity amido carboxylic acid comprises least about 90%, preferably about 95%, even more preferably about 97% by weight, of an amido carboxylic acid of the formula:

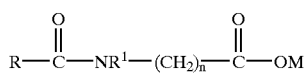

wherein R is $C_5$–$C_{21}$ hydrocarbyl, $R^1$ is selected from hydrogen and $C_1$–$C_3$ alkyl, and n is an integer from about 1 to about 8, M is H or an alkali metal salt; and less than about 10% by weight of color forming bodies; wherein the process is performed in the presence of less than about 10 ppm, preferably less than about 5 ppm, more preferably less than about 2 ppm, even more preferably less than about 0.5 ppm of transition metals, preferably selected from the group consisting of iron, nickel, chromium and mixtures thereof, more preferably iron, nickel, and mixtures thereof, with an acid halide to prepare the corresponding amido acid halide; and (b) reacting the amido acid chloride of step (a) with a phenolsulfonate salt.

According to a third aspect to provide 4-sulfophenyl-[(1-oxyalkanoyl)amino]alkanoate when prepared according to either the first or second aspect of the present invention.

According to a fourth aspect to provide cleaning compositions comprising 4-sulfophenyl-[(1-oxyalkanoyl)amino] alkanoate prepared according to either the first or second aspect of the present invention.

Accordingly, it is an aspect of the present invention to provide a process for preparing a 4-sulfophenyl-[(1-oxyalkanoyl)amino]alkanoate. It is yet another aspect of the present invention to provide flexibility to a process for preparing a 4-sulfophenyl-[(1-oxyalkanoyl)amino] alkanoate. These, and other aspects, features and advantages of the present invention will be recognizable to one of ordinary skill in the art from the following description and the appended claims.

All percentages, ratios and proportions herein are on a weight basis unless otherwise indicated. All documents cited herein are hereby incorporated by reference.

DETAILED DESCRIPTION OF THE PREFERRED EMBODIMENTS

The process of the present invention for preparing amido acid phenyl ester sulfonates involves as an important feature limiting the amount of transition metals and color forming bodies present in the process. As earlier noted, it is the reduction of the transition metals and color forming bodies content in the process which leads to the benefits and advantages of the present invention.

According to a first aspect of the present invention, a process for the preparation a 4-sulfophenyl-[(1-oxyalkanoyl)amino]alkanoate is provided. The process comprises the steps of:

reacting an acetoxy benzene sulfonate salt with a high purity amido carboxylic acid, wherein said high purity amido carboxylic acid comprises least about 90%, preferably about 95%, even more preferably about 97% by weight, of a amido carboxylic acid of the formula:

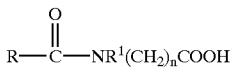

wherein R is $C_5$–$C_{21}$ hydrocarbyl, preferably $C_5$–$C_{14}$ hydrocarbyl, more preferably $C_6$–$C_{12}$ alkyl, $C_6$–$C_{12}$ alkenyl, even more preferably $C_6$–$C_{10}$ alkyl, $R^1$ is selected from hydrogen and $C_1$–$C_3$ alkyl, preferably H, methyl, more preferably methyl, and n is an integer from about 1 to about 8; preferably an integer from about 2 to about 7, more preferably an integer from about 3 to about 6 and less than about 10%, preferably less than about 5%, more preferably less than about 2%, even more preferably less than about 1% by weight, of color forming bodies;

wherein the process is performed in the presence of less than about 10 ppm, preferably less than about 5 ppm, more preferably less than about 2 ppm, even more preferably less than about 0.5 ppm of transition metals, preferably selected from the group consisting of iron, nickel, chromium and mixtures thereof, more preferably iron, nickel, and mixtures thereof.

It is preferred that the high purity amido carboxylic acid comprises least about 95%, more preferably 97%, of a amido carboxylic acid of the formula:

The total impurities indicated above negatively influence the ability to effectively recrystallize the product due to the impurities drawing product into the filtrate/centrate by serving as hydrotropes. In addition, it is important to have less than 1%, less than 0.5%, less than 0.1% of total aminoalkanoic acid and cyclic lactam.

Preferably, the high purity amido carboxylic acid is produced by the reaction of a carboxylic acid of the formula:

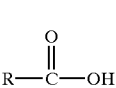

wherein R is $C_5$–$C_{21}$ hydrocarbyl; with a lactam of the formula:

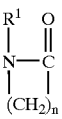

wherein $R^1$ is selected from hydrogen and $C_1$–$C_3$ alkyl, and n is an integer from 1 to 8. Suitable lactam monomers include butyrolactam, valerolactam, epsilon-caprolactam, beta propiolactam, delta valerolactam, and similar lactams. These lactams may be substituted at the nitrogen atom by hydrocarbon radicals containing one to three carbon atoms, for example, methylcaprolactam. Epsilon-caprolactam and suitable derivatives thereof are the preferred lactam monomers.

The carboxylic acid contains an aliphatic, such as a straight or branched chain, or aliphatic radical, cycloaliphatic or hydroaromatic radical. The carboxylic acid has from about 6 to about 22 carbon atoms, preferably about 8 to about 20 carbon atoms, and most preferably from about 7 to about 10 carbon atoms. These radicals may be connected to the carboxyl group through an aromatic radical. The carboxylic acids may be straight or branched chain fatty acids of natural or synthetic origin which may be of a saturated or unsaturated nature. The carboxylic acids may be used in pure form or else in the form of their mixtures.

Suitable examples of carboxylic acids and esters are: Caprylic acid, methyl caprylate, pelargonic acid, methyl pelargonate, capric acid, methyl caprate, isopropyl caprate, undecylic acid, lauric acid, palmitic acid, stearic acid, oleic acid, linoleic acid, behenic acid, teraphthalic acid, dimethyl teraphthalate, phthalic, isophthalic acid, napthene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. Preferred carboxylic acids are capric and capryltic.

Preferably, the process is performed in the presence of a polar aprotic reaction solvent such as dialkylacetamides, such as, N,N-dimethylacetamide; dialkyl sulfoxide wherein the alkyl group has one to six carbon atoms such as dimethyl sulfoxide; dimethyl ethers of diethylene glycol such as triglyme; cyclic or acyclic alkyl sulfones wherein the alkyl group has one to six carbon atoms such as tetrahydrothiophene-1,1-dioxide; and halogenated aromatic solvents such as dichlorobenzene and trichlorobenzene; and alkyl substituted aromatic solvents where the alkyl groups contain one to six carbon atoms such as triisopropylbenzene. Preferably, the reaction solvent is tetrahydrothiophene-1,1-dioxide.

It is preferred that the process is conducted at a temperature of from about 120° C. to about 220° C.

Preferably the process may contain a transesterification catalysts. Such catalysts include tertiary amine catalysts, alkali metal salts, metallic catalysts, acidic catalysts, and combinations thereof. Specific examples of catalysts for use in the present invention include: dimethyl aminopyridine, imidazole, sodium acetate, sodium hydroxide, and titanium tetraisopropoxide. The transesterification catalyst(s) is added in an amount of about 0.01 to about 0.3 mole, preferably about 0.1 to about 0.3 mole equivalent of the acetoxy benzene sulfonate salt.

The process for preparing a 4-sulfophenyl-[(1-oxyalkanoyl)amino]alkanoate by reacting an acetoxy benzene sulfonate salt with a high purity amido carboxylic acid preferably comprises the steps of:

(a) reacting an alkali metal salt of 4-hydroxybenzene sulfonic acid with a $C_2$ to $C_4$ carboxylic anhydride at a sufficient temperature and time in a reaction solvent to form a reaction mixture having an alkali metal salt of 4-acyloxybenzenesulfonic acid and a $C_2$ to $C_4$ carboxylic acid, wherein the alkali metal salt of 4 hydroxybenezene sulfonic acid and $C_2$ to $C_4$ carboxylic anhydride are present in a mole ratio of 1:1 to 1:40, respectively, and the reaction solvent is present in a weight ratio of 1:1 to 20:1 based on the weight of the alkali metal salt of 4-hydroxybenzene sulfonic acid, provided that excess carboxylic anhydride is removed under reduced pressure from the reaction vessel;

(b) adding a [(1-oxyalkanoyl)amino]alkanoic acid and at least one transesterification catalyst to said reaction mixture and heating at a temperature of from about 120° C. to about 220° C. for from about 0.5 to about 10 hours and a pressure sufficient to maintain reflux of said reaction solvent and to remove the $C_2$ to $C_4$ carboxylic acid from the reaction vessel, to form a reaction product containing a salt of 4-sulfophenyl-[(1-oxyalkanoyl)amino]alkanoate wherein the moles of the [(1-oxyalkanoyl)amino]alkanoic acid added is 0.7 to 5 times the moles of the alkali metal salt of 4-hydroxybenzene sulfonic acid;

(c) admixing said reaction product including reaction solvent and a salt of 4-sulfophenyl-[(1-oxyalkanoyl)amino]alkanoate with a water-based purification system to form a purification mixture, said water-based purification system including a processing aid and having water present at a ratio of 4-sulfophenyl-[(1-oxyalkanoyl)amino]alkanoate to water ranging from about 1:0.05 to about 1:50;

(d) separating a purified salt of 4-sulfophenyl-[(1-oxyalkanoyl)amino]alkanoate from said purification mixture; and (e) collecting the salt of 4-sulfophenyl-[(1-oxyalkanoyl)amino]alkanoate.

The preparation of the 4-sulfophenyl-[(1-oxyalkanoyl)amino]alkanoate according to the second aspect involves two basic steps and is fully described in U.S. Pat. No. 5,466,840, the disclosure of which is herein incorporated by reference. In the first step, a salt, such as an alkali metal salt, of 4-hydroxybenzenesulfonic acid is reacted with a $C_2$ to $C_4$ carboxylic anhydride preferably at a temperature of 50° C. to 200° C. for 0.5 to 5 hours in a reaction solvent to form a reaction mixture having a salt of 4-acyloxybenzenesulfonic acid and a $C_2$ to $C_4$ carboxylic acid. Preferably, the reaction is conducted at a temperature of 110° C. to 170° C. for 1 to 2 hours. Preferably, the salt is an alkali metal salt and may be any alkali metal such as sodium and potassium, or alternatively another salt such as calcium, magnesium or ammonium. However, sodium is the most preferred.

Preferably, when present, the $C_2$ to $C_4$ carboxylic anhydride is present in an amount of from about 1 to about 40 moles per mole of the salt of 4-hydroxybenzenesulfonic acid, preferably about 1 to about 5 moles, and most preferably about 1 to about 1.3 moles. Examples of suitable $C_2$ to $C_4$ carboxylic anhydrides are acetic anhydride, propionic anhydride, butyric anhydride, and isobutyric anhydride with acetic anhydride being the most preferred.

Preferably, when the process involves the reaction of an alkali metal salt of 4-hydroxybenzene sulfonic acid with a $C_2$ to $C_4$ carboxylic anhydride, namely the second aspect of the present invention, the reaction solvent is present in a ratio of reaction solvent to the salt of 4-hydroxybenzenesulfonic acid of about 1:1 to about 20:1, preferably about 4:1 to about 6:1 weight ratio.

A processing aide may be added to the water-based purification system to, among other reasons, enhance separation and reduce foaming in the process. The processing aide is selected from the group consisting of linear or branched $C_1$ to $C_6$ alcohols or diols, linear or branched $C_1$ to $C_6$ ketones, linear or branched $C_1$ to $C_6$ acids, linear or branched $C_1$ to $C_6$ esters, cyclic or acyclic $C_1$ to $C_6$ ethers, linear or branched, cyclic or acyclic $C_1$ to $C_6$ sulfoxides and sulfones and mixtures thereof. Most preferably, the processing aide is selected from the group consisting of methyl alcohol, ethyl alcohol, propyl alcohol, isopropyl alcohol, acetone, acetic acid and mixtures thereof with isopropyl alcohol being the most preferred.

Upon completion of the transesterification reaction and the formation of the salt of 4-sulfophenyl-[(1oxyalkanoyl)amino]alkanoate, the reaction solvent may be removed in an optional step. The removal of solvent is accomplished by either an evaporative process such as distillation or drying, or by crystallization followed by filtration. Removal of the solvent is conducted at low vacuum and at a temperature at which vaporization of the solvent occurs. Preferably, the vacuum range is from about 0.5 absolute to about 100 mm Hg, and the temperature range is from about 100° C. to about 230° C. The upper end of the temperature range has the advantage of more rapid solvent removal, whereas the lower end of the temperature range has the advantage of reducing high temperature-promoted product decomposition and the associated increase in color and impurities. Preferably, at least about 90% and more preferably at least about 95% of the solvent is removed. Of course, it is important to note that this removal of solvent is entirely optional in the present invention as the water-based purification system may operate in the presence of large amounts of reaction solvent.

Removal of the co-carboxylic acid can be achieved via distillation or by sparging with an inert gas such as nitrogen. Additional reaction solvent may be added in the transesterification step to maintain a fluid reaction mixture . The moles of [(1-oxyalkanoyl)amino alkanoic acid added is about 0.7 to about 5 times the moles of the salt of 4-hydroxybenzenesulfonic acid used in the first step.

The [(1-oxyalkanoyl)amino alkanoic acid is prepared by routes which are well known in the art and disclosed for example in U.S. Pat. Nos. 5,391,780; 5,414,099; 5,534,642; 5,153,541; 5,650,527; 5,286,879 and 5,523,434, the disclosures of which are herein incorporated by reference. A preferred synthesis for the [(1-oxyalkanoyl)amino alkanoic acid is an amidation reaction involving reacting a nitrogen compound selected from a lactam and an amino acid with a carboxylic acid or ester. Preferably, the [(1-oxyalkanoyl)amino alkanoic acid is 6-[(1-oxyoctyl)amino hexanoic acid, 6-[(1-oxynonyl)amino hexanoic acid, 6-[(1-oxydecyl)amino hexanoic acid or mixtures of the three.

The reaction product including the salt of 4-sulfophenyl-[(1-oxyalkanoyl)amino]alkanoate is admixed with a water-based purification system to yield the purified salt of the present invention. The water-based purification system, of course, includes at least a minimum amount of water. However, other ingredients such as processing aids may be included in the system.

The water-based purification system has a minimum amount of water such that the ratio of 4-sulfophenyl-[(1- oxyalkanoyl)amino]alkanoate to water ranges from about 1:0.05 to about 1:50. More preferably, the ratio of salt of 4-sulfophenyl-[(1-oxyalkanoyl)amino]alkanoate to water ranges from about 1:0.1 to about 1:40. As discussed earlier, the reaction solvent does not need to be removed from the reaction product of the salt of 4-sulfophenyl-[(1-oxyalkanoyl)amino]alkanoate synthesis. In such instances, wherein at least about 10%, and more preferably at least about 20% and more preferably at least about 40% of the reaction solvent remains, a lower amount of water is required in the system. In such cases, the ratio of 4-sulfophenyl-[(1-oxyalkanoyl)amino]alkanoate to water preferably ranges from about 1:0.1 to about 1:40. When the reaction solvent is optionally removed as described hereinbefore, a larger percentage of water may be necessary in the purification system. In such instances, the ratio of 4-sulfophenyl-[(1-oxyalkanoyl)amino]alkanoate to water ranges from about 1:1 to about 1:50.

In highly preferred scenarios, the processing aide is miscible with water and has a density of less than or equal to the preferred reaction solvent, tetrahydrothiophene-1,1-dioxide so as to increase the density difference between the product salt and the purification system thereby increasing the ease of removal of the salt. The solvent tetrahydrothiophene-1,1-dioxide has a density of 1.216 gm/cm$^3$. The processing aide is typically present in the purification system at a ratio of 4-sulfophenyl-[(1-oxyalkanoyl)amino]alkanoate to processing aide ranging from about 1:0.1 to about 1:50 and most preferably from about 1:1 to about 1:20. The amount of processing aide employed is mainly dependent on the physical properties desired. The lower end can be chosen to minimize foaming (although less is also needed when reaction solvent which also reduces foaming is present). The upper end is typically chosen for convenience during product recovery such as filtering or centrifuging. When a processing aide is used in conjunction with the water-based purification system, product yields from recrystallization are typically greater than about 75%, more preferably 85%, and most preferably 90%.

As discussed earlier, the water-based purification system provides increased flexibility to the prior art processes by allowing recovery of product salt from either a slurry or a homogeneous solution. That is, in a typical process the step of admixing reaction product salt with the purification system with or without processing aide as described hereinbefore yields either a slurry or homogeneous solution of formed product salt. The purification may be conducted on this slurry or homogeneous solution at room or slightly elevated temperatures to remove impurities and color forming bodies. However, the admixing step may also in optional embodiments involve heating the admixture from about 30° C. to about 100° C. to form a slurry or homogenous solution of product salt. The product salt may then be recovered from this homogenous solution or slurry to yield a highly purified product salt. The use of a homogenous solution or slurry provides flexibility and a controlled recrystallization of the product salt to impart various desired results.

The next step of the process involves the separation of the purified salt of 4-sulfophenyl-[(1-oxyalkanoyl)amino]alkanoate from the water-based purification system and any remaining solvent. This separation may be accomplished by methods which are well-known in the art such as centrifugation or filtration. The filtrate from this separation step may include reaction solvent, water and processing aides, if present, which can be individually recovered and recycled to their respective steps. If desired, the purified salt may be dried by any conventional drying technique such as a ring drier or vacuum oven. It is important to note that the purification with the water-based system and separation of the product may be repeated as necessary until a salt of 4-sulfophenyl-[(1- oxyalkanoyl)amino]alkanoate of the desired purity is obtained. Depending upon the purity of the starting materials, greater than about 80% and preferably about 90% yield of product may be obtained in the process of the present invention.

The processes as described herein may be conducted stepwise as a batch process or on a continuous basis. The salt of 4-sulfophenyl-[(1-oxyalkanoyl)amino]alkanoate product, preferably, has the general formula RC(O)N(R$^1$)(CH$_2$)$_n$C(O)—OBS where R represents C$_5$–C$_{21}$ alkyl, C$_5$–C$_{21}$ alkenyl, R$^1$ represents hydrogen or methyl; n is an integer from about 1 to about 8; and —OBS is an oxybenzenesulfonate leaving group. Preferably, the purified salt of 4-sulfophenyl-[(1-oxyalkanoyl)amino]alkanoate is sodium 4-sulfophenyl-6-[(1-oxynonyl)amino]hexanoate, wherein R is C$_8$H$_{17}$, n is 5 and or sodium 4-sulfophenyl-6-[(1-oxydecyl)amino]hexanoate wherein R is C$_9$H$_{19}$, n is 5. The product may also include mixtures of compounds.

According to a second aspect of the present invention, the process for preparing a 4-sulfophenyl-[(1-oxyalkanoyl)amino]alkanoate comprises the steps of:

(a) reacting a high purity amido carboxylic acid, wherein said high purity amido carboxylic acid comprises least about 90% ,preferably about 95%, even more preferably about 97% by weight, of an amido carboxylic acid of the formula:

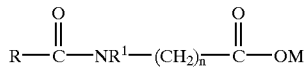

wherein R is C$_5$–C$_{21}$ hydrocarbyl, preferably C$_5$–C$_{14}$ hydrocarbyl, more preferably C$_6$–C$_{12}$ alkyl, C$_6$–C$_{12}$ alkenyl, even more preferably C$_6$–C$_{10}$ alkyl, R$^1$ is selected from hydrogen and C$_1$–C$_3$ alkyl, preferably H, methyl, more preferably methyl, and n is an integer from about 1 to about 8; preferably an integer from about 2 to about 7, more preferably an integer from about 3 to about 6, M is H or an alkali metal salt; and less than about 10%, preferably less than about 5%, more preferably less than about 2%, even more preferably less than about 1% by weight of color forming bodies;

wherein said process is performed in the presence of less than about 10 ppm, preferably less than about 5 ppm, more preferably less than about 2 ppm, even more preferably less than about 0.5 ppm of transition metals, preferably selected from the group consisting of iron, nickel, chromium and mixtures thereof, more preferably iron, nickel, and mixtures thereof; and (b) reacting the amido acid chloride of step (a) with a phenolsulfonate salt. Preferably the high purity amido carboxylic acid comprises least about 95%, of a amido carboxylic acid of the formula:

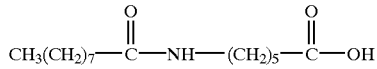

The process according to the second aspect of the invention can be conducted in the presence of water or in the absence of water. Preferably, when the process is conducted in the presence of water it is conducted in a two-phase reaction medium comprising water and an organic solvent which is compatible with the amido acid halide formed in step (a). Alternatively the process may be conducted in the presence of an organic solvent which is compatible with the amido acid halide formed in step (a).

Preferably the acid halide is an inorganic acid halide selected from the group consisting of $PCl_3$, $PCl_5$, $POCl_3$, and their corresponding bromides, or oxalyl chloride, more preferably the acid halide is $SOCl_2$, $PCl_3$, $PCl_5$, $POCl_3$, even more preferably $SOCl_2$. It is preferred that the acid halide be present in the process at about greater than or equal to 1 mole equivalent.

Color Forming Bodies

It has now been surprisingly found that a high purity amido acid phenyl ester sulfonates can be formed with minimal, preferably free of, colored impurities. There are several key aspects to minimizing the formation of colored impurities in the final product. They are (i) minimizing the amount of color forming bodies in the starting materials; (ii) minimizing the amount of transition metals present in the reaction; (iii) using high purity amido carboxylic acid; (iv) minimizing amount of oxygen present in the synthesis of starting materials and products; (v) minimizing exposure of amido carboxylic acid to high temperature; and (vi) minimizing exposure of final product to high temperatures when solvent concentration is low (concentration less than about 1:1 ratio of sulfolane to product). All six or any possible combinations thereof of these conditions can produce a final crude product of acceptable color.

(i) Minimizing the Amount of Color Forming Bodies—In the present invention there is less than about 10%, preferably less than about 5%, more preferably less than about 2%, even more preferably less than about 1%, by weight of color forming bodies present in the starting materials. These color forming bodies are believed to be amido acid which has decomposed or is the product of some side reaction produced during the formation of the amido acid. It is believed, while not wishing to be limited by theory, that both intramolecular and intermolecular decomposition of the amido carboxylic acid result in the formation of the color forming bodies. The intramolecular mechanism decomposition is believed to result in formation of caprolactam and nonanoic acid, while intermolecular mechanism decomposition is believed to result in formation of 6-aminocaproic acid and amido acid oligomers. One possible mechanism for color formation is:

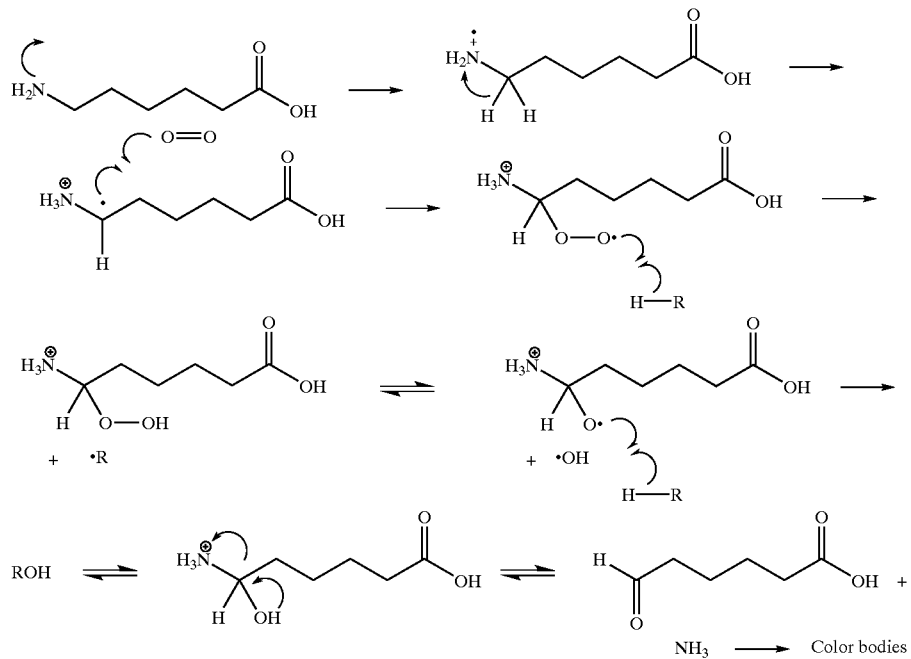

(ii) Minimizing the Amount of Transition Metal—The process of the present invention is performed in the presence of less than about 10 ppm, preferably less than about 5 ppm, more preferably less than about 2 ppm, even more preferably less than about 0.5 ppm of transition metals, preferably selected from the group consisting of iron, nickel, chromium and mixtures thereof, more preferably iron, nickel, and mixtures thereof. It has now been found that even trace amounts, i.e. greater than 10 ppm of transition metal, can result in a product with a poor color, because of increased formation of color forming bodies by the transition metal. Additionally, when oxygen is present in combination with a transition metal, such as iron or nickel, a product is formed with even worse color than the product formed with just transition metal present. The transition metal is believed to act as a catalyst, optionally in combination with oxygen, in the breakdown of the amido acid to form the color forming bodies. That is, one possible mechanism, where the transition metal is, for, example iron is:

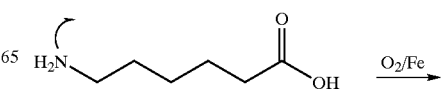

-continued

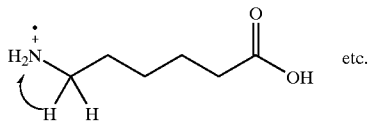
etc.

By transition metal, it is meant that all possible oxidation states of transition metals are included, for example $Fe^{2+}$ and $Fe^{3+}$.

There are many possible ways or reducing and even eliminating transition metals from the present process. Examples include minimizing the contact of the reaction with transition metals such as, by the use of glass line reactors, recrystallizing the high purity amido carboxylic acid, transferring the high purity amido carboxylic acid as a solid, using distilled material immediately rather than storing in metal tanks, and the use of chelants.

(iii) High Purity Amido Carboxylic Acid—The process of the present invention is performed using a high purity amido carboxylic acid which comprises least about 90%, preferably about 95%, even more preferably about 97% by weight, of a amido carboxylic acid of the formula:

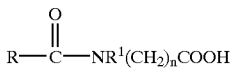

wherein R is $C_5$–$C_{21}$ hydrocarbyl, $R^1$ is selected from hydrogen and $C_1$–$C_3$ alkyl, and n is an integer from about 1 to about 8. The use of amido carboxylic acid other that high purity amido carboxylic acid results in the formation of a product with poor color. When the amido carboxylic acid is kept molten for extended (or even modest or short) periods of time, the rate at which these color bodies form is greatly increased. It is believed that heat increases the following reaction:

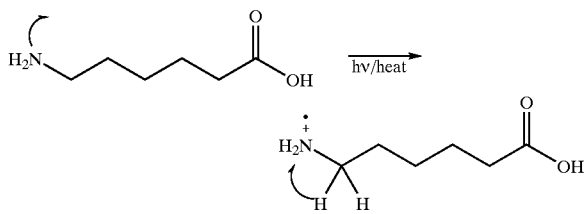

as well as the reaction which forms the aminoalkanoic acid and cyclic lactam.

Also, slow decomposition of amido acid to fatty acid, lactam and 6-aminocaproic acid adds to the possibility of further color bodies forming over time. Darker crude product requires more water to remove color (if it can be removed), and may require additional purification steps, both of which lead to increased product loss to the filtrate. Consequently, it is preferred to minimize the time that the amido carboxylic acid is heated and or remains molten. A diluent can also be used to decrease the melting point of the amido carboxylic acid. Such diluents may include solvents such as sulfolane or acetic acid.

When necessary recrystalization can be done on the crude amido carboxylic acid. Recrystallization of the amido acid with a solvent such as, an alcohol solvent with or without water, leads to amido carboxylic acid of sufficient purity to be suitable for use in the production of 4-sulfophenyl-[(1-oxyalkanoyl)amino]alkanoate. While not wishing to be limited by theory it is believed that the recrystalization reduces the amount of cyclic lactam and aminoalkanoic acid to be <1.0%. However, it is preferred to prepare a amido carboxylic acid which does not require any further purification steps and will produce a 4-sulfophenyl-[(1-oxyalkanoyl)amino] alkanoate of acceptable purity and color.

(iv) Minimizing the Amount of Oxygen—The process of the present invention is performed keeping the level of residual oxygen at a minimum. Minimizing oxygen is accomplished by use of vacuum, inert gas blanket or sparge. If oxygen is present in the storage of the reagents and/or in the synthesis of the bleach activator color formation is probable. Low oxygen levels slow the color formation process, especially in the absence of transition metals such as iron or nickel.

(v) Minimizing exposure of amido carboxylic acid to high temperature—Even in the absence of transition metals and oxygen, the amido carboxylic acid can undergo decomposition if exposed to high temperatures. For instance the purity of recrystallized amido carboxylic acid is reduced from 97.7% to 83.9% in only 3 hours at 165° C. and down to 39.5% in 18 h. Decomposition at a rate of about 1% per day is also observed at temperatures below 100° C., even in the presence of an argon atmosphere. As mentioned earlier, air exposure as well as the presence of transition metals does increase color formation. Overall, temperature, time and air all play a key role in color formation.

Typically, the solid amido acid will be stored at room temperature, to minimize the exposure of the amido acid to high temperature. If necessary the solid could be kept at higher temperature, about 70° C., if there was a reason to do so with minimal decomposition. If stored in molten form (for convenience associated with pumping, etc.) then the decomposition of the amido carboxylic acid will occur over time. Other factors such as, purity of material, transition metal content, exposure to air/oxygen, etc., become significant. For example, the color of the amido acid does not change noticeably in 3 hours at 105° C. if the molten amido acid is stored under an argon blanket. If exposed to air at this temperature the color formation is obvious in 3 hours. Regardless, both the amido acid kept under argon and that kept under argon and exposed to air produce a final product with an unacceptable color. At some point the color forming bodies formed in 3 hours at 105° C under the argon blanket will result in real color in the final crude product. Even without exposure to air, color bodies do form when the acid is kept molten for prolonged periods of time. For this is the reason it is preferred to store the amido acid as a solid or minimizing time under molten conditions. Furthermore, it may be the case that any time spent in the molten form is harmful to the final product color.

If necessary storage of the molten material is possible, but the material must be kept molten at a lower temperature, such as 85° C. This will result in much less apparent decomposition, typically a loss of activity much less than 1% per day or even per week. However, it is believed that this low temperature molten material will accumulate color forming bodies if not properly cared for. That is minimizing the transition metal content, and oxygen content, etc. A small amount of aminoalkanoic acid can produce a significant amount of forming color bodies.

One possible intermolecular mechanism for the formation of nonanoic acid, amido acid dimers and consequently to color forming bodies:

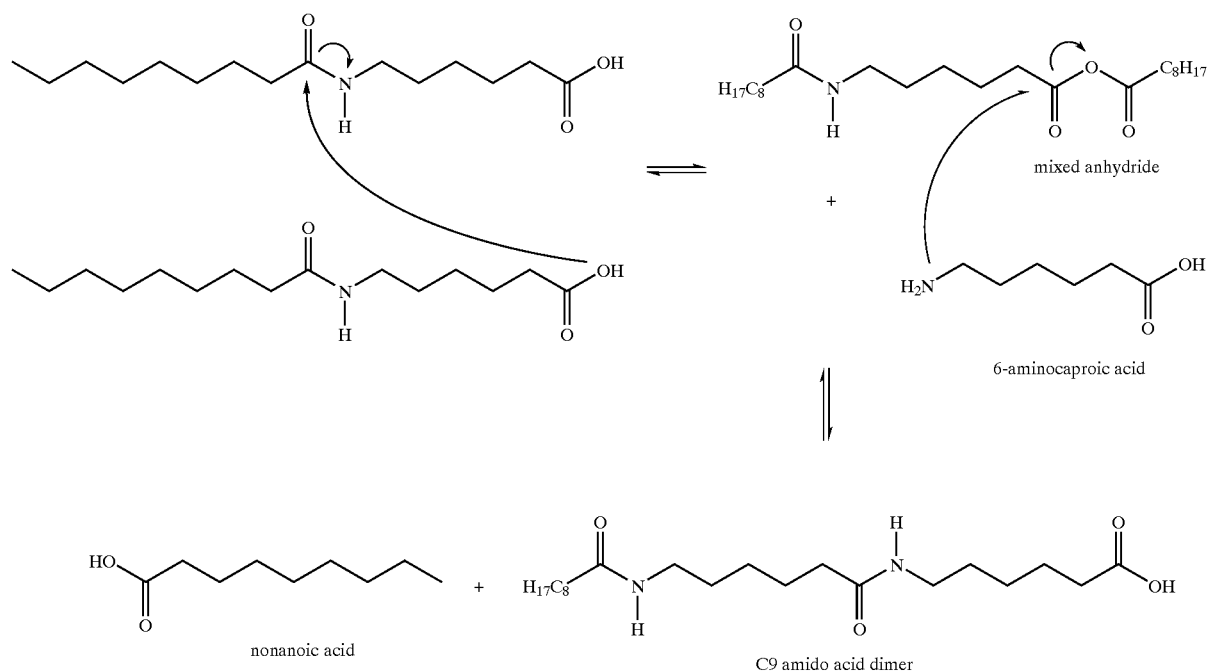
OR another possible mechanism for the generation of 6-aminocaproic acid and caprolactam via intramolecular mechanism and consequently to color forming bodies.
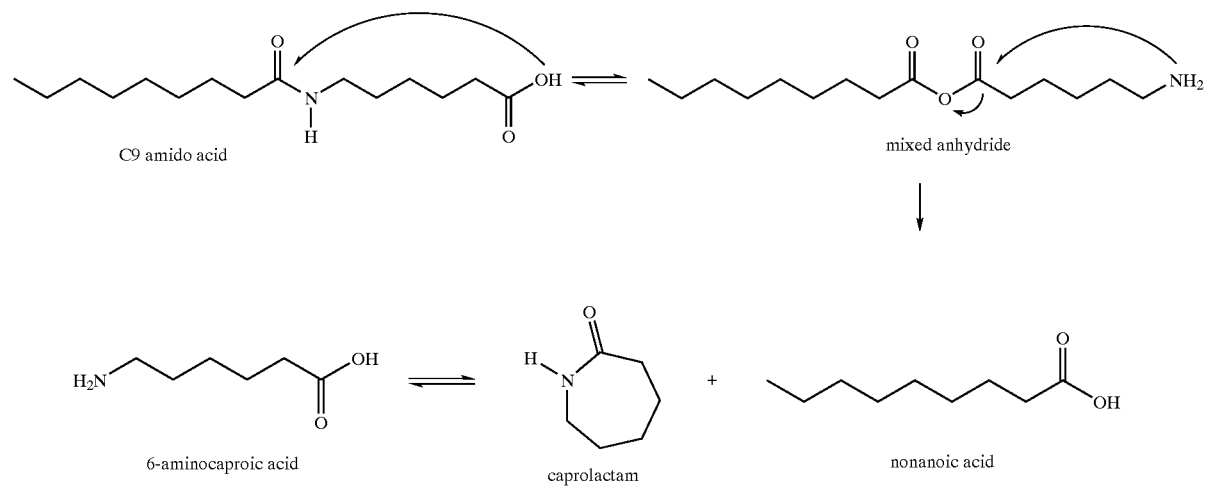

(vi) Minimizing exposure of final product to high temperatures when solvent concentration is low—(concentration less than about 1:1 ratio of sulfolane to product). This is important when trying to remove solvent from product (if water purification method not utilized). Decomposition and color formation can reach several percent per hour at temperatures above 190 deg C., particularly under high vacuum and when exposed to air.

Intermolecular Mechanism

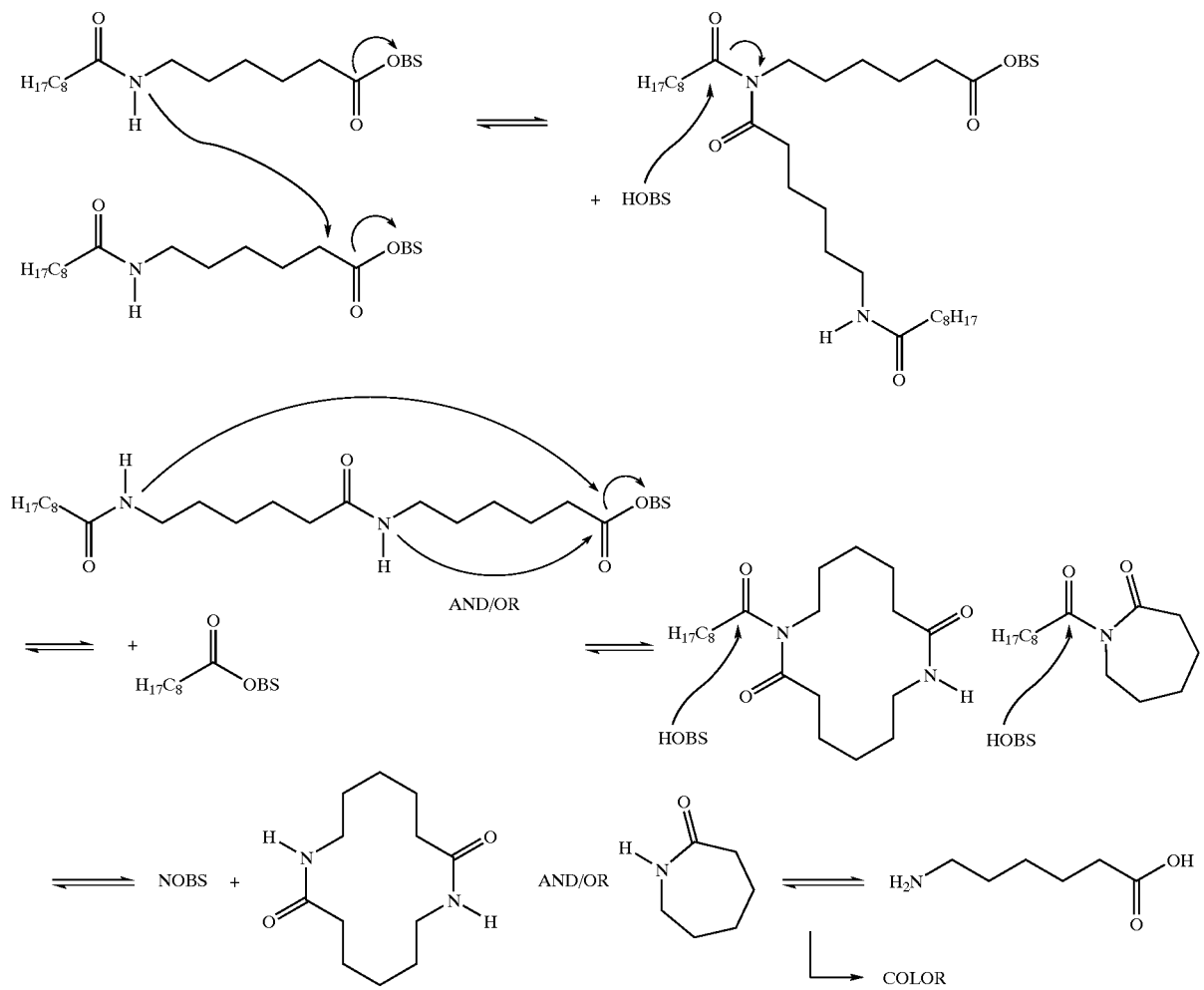

OR another possible mechanism for the generation of 6-aminocaproic acid and caprolactam.

Intramolecular Mechanism

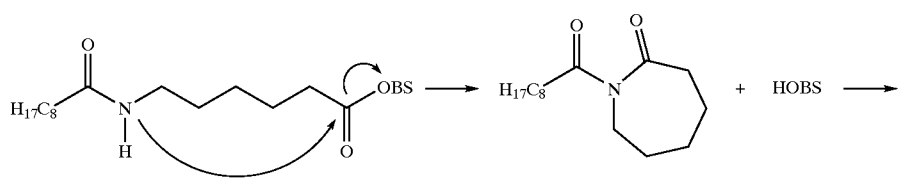

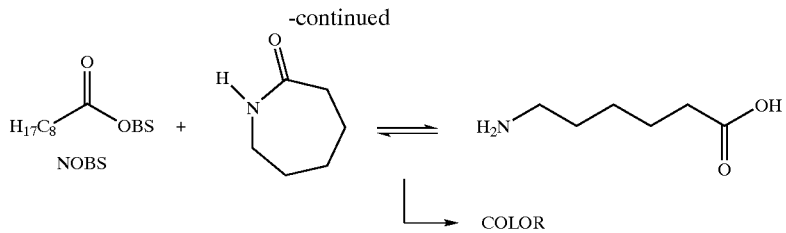

It is also worth noting that some of the possible byproducts are activators in there own right. For example:

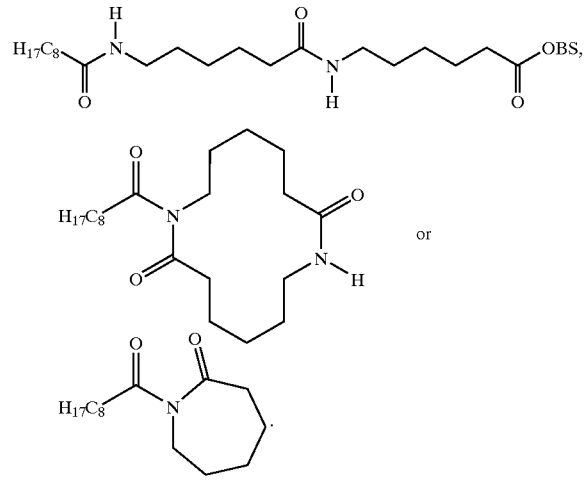

However as it is believed that these byproducts are intermediates in the production of the color forming bodies, it is preferred to not only minimize their content in the intermediates and product, but also to minimize their formation.

The process of the present invention will be further illustrated by a consideration of the following examples, which are intended to be exemplary of the invention.

EXAMPLES

Examples 1–7

Preparation of Sodium Salt of 4-sulfophenyl-6-[(1-oxynonyl)amino]hexanoate

A dry 500 mL 3-necked round-bottomed flask equipped with an overhead stirrer (mechanical), condenser with attached Dean Stark apparatus, addition funnel, Argon source, and oil bath with temperature controller is charged with 35.6 g of tetrahydrothiophene-1,1-dioxide and heated to 80° C. To the reaction flask is added 178 mg (2.16 mmol) of sodium acetate, 7.03 g (0.036 mol) of sodium 4-hydroxybenzenesulfonate, and 9.47 g (0.035 mol) of 6-[(1-oxynonyl)amino hexanoic acid (see Table I for metal content and purity of starting material). The mixture is heated to 140° C. To the reaction is added (via addition funnel) 4.07 mL (0.043 mol) of acetic anhydride over 30–40 min at 140° C. The pressure is then reduced to 15 mm Hg, and as the temperature is raised to 165° C. over a period of 20–30 min, low boiling materials flash over and are collected. The temperature is maintained at about 165° C. (15 mm Hg) for 5 h. After the five hour reaction time, a crude reaction mixture containing the sodium salt of 4-sulfophenyl-[(1-oxynonyl)amino]hexanoate is obtained. The preparation is represented by the following reaction:

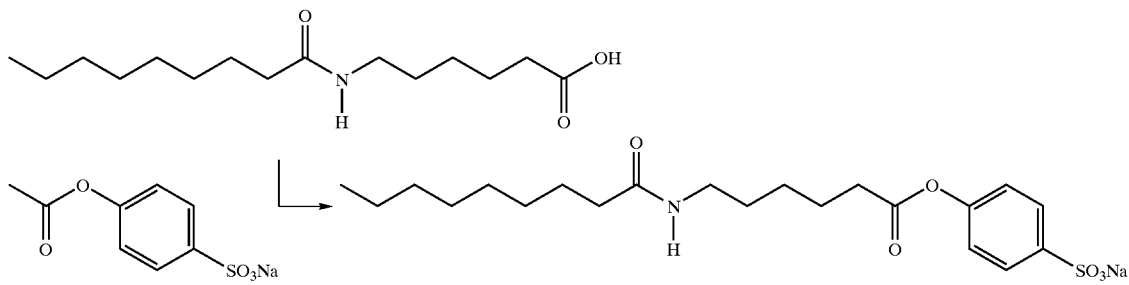

Experiment 1: The crude reaction mixture is transferred to a mechanically stirred solution of 60 grams of isopropyl alcohol. The resulting mixture (slurry) is warmed to 40° C. The solution is stirred and centrifuged to obtain a solid, which is transferred to a mechanically stirred solution of 30 grams of isopropyl alcohol, stirred, and centrifuged to obtain a solid which is again washed with 30 grams of isopropyl alcohol and dried under vacuum to give 4-sulfophenyl-[(1-oxynonyl)amino]hexanoate. Data on the starting material and product prior to and after purification is summarized in Table I, entry 1. Experiments 2–7: The crude reaction mixture is transferred to a mechanically stirred solution of water (4.5 g for entry 2, 12 g for entry 3, and 15 g for entries 4, 6, and 7) and 60 grams of isopropyl alcohol. The pH is adjusted to 5.5, and the resulting mixture is warmed to 75° C. The solution is stirred and cooled to 25° C. over a period of 3 hours. The mixture is filtered to obtain a solid. The solid is washed 3 times with 30 grams of isopropyl alcohol and dried under vacuum to give 4-sulfophenyl-[(1-oxynonyl) amino]hexanoate. Data on the starting material and product prior to and after purification is summarized in Table I, entry 4, 6 and 7.

Example 8

Preparation of Sodium Salt of 4-sulfophenyl-7-[(1-oxyoctyl- 1-methyl)amino]heptanoate A dry 500 mL 3-necked round-bottomed flask equipped with an overhead stirrer (mechanical), condenser with attached Dean Stark apparatus, addition funnel, Argon source, and oil bath with temperature controller is charged with 35.6 g of tetrahydrothiophene-1,1-dioxide and heated to 80° C. Argon sparge of all reagents and reaction vessels is performed so as to avoid the introduction of air (oxygen) during all parts of the reaction. To the reaction flask is added 178 mg (2.16 mmol) of sodium acetate, 7.03 g (0.036 mol) of sodium 4-hydroxybenzenesulfonate, and 10.0 g (0.035 mol) of the sodium salt of 6-[(1-oxyoctyl-1-methyl)amino] heptanoic acid (see Table I for metal content and purity of starting material). The mixture is heated to 140° C. To the reaction is added (via addition funnel) 4.07 mL (0.043 mol) of acetic anhydride over 30–40 min at 140° C. The pressure is then reduced to 15 mm Hg, and as the temperature is raised to 165° C. over a period of 20–30 min, low boiling materials flash over and are collected. The temperature is maintained at about 165° C. (15 mm Hg) for 5 h. After the five hour reaction time, a crude reaction mixture containing the sodium salt of 4-sulfophenyl-7-[(1-oxyoctyl-1-methyl) amino]heptanoate is obtained. The crude reaction mixture is transferred to a mechanically stirred solution of 15 g of water and 60 grams of acetone. The pH is adjusted to 5.5, and the resulting mixture is warmed to 45° C. The solution is stirred and cooled to 25° C. over a period of 1 h. The mixture is filtered to obtain a solid. The solid is washed 3 times with 30 grams of acetone and dried under vacuum to give the sodium salt of 4-sulfophenyl-7-[(1-oxyoctyl-1-methyl)amino]heptanoate. Data on the starting material and product prior to and after purification is summarized in Table I, entry 8. The preparation is represented by the following reaction:

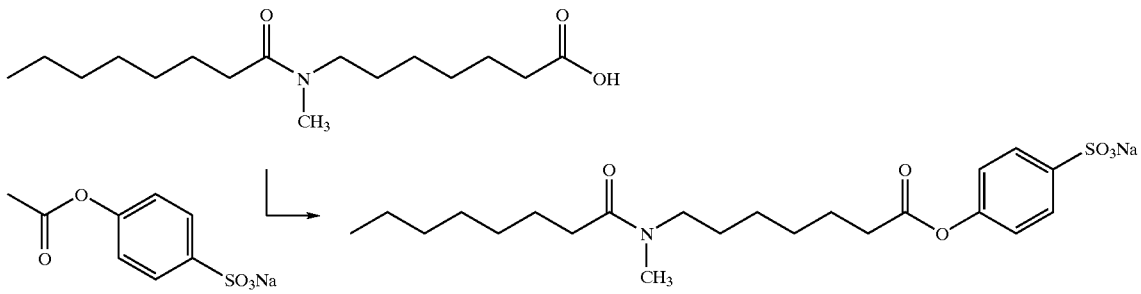

Example 9

Preparation of Sodium Salt of 4-sulfophenyl-7-[(1-oxyoctyl- 1-methyl)amino]heptanoate The same procedure as used as in example 8 with the exception that during the reaction period of 5 h during which the temperature is maintained at about 165° C. (15 mm Hg), an air leak is allowed to occur for 5 min out of each hour, during which time the pressure is close to atmospheric. The same workup procedure is used to give the sodium salt of 4-sulfophenyl-7-[(1-oxyoctyl-1-methyl)amino]heptanoate. Data on the starting material and product prior to and after purification is summarized in Table I, entry 9.

Example 10

Preparation of Sodium Salt of 4-sulfophenyl-7-[(1-oxyoctyl-1-methyl)amino]heptanoate The same procedure as used as in example 8 with the exception that the workup procedure is altered as follows: The crude solvent-containing reaction mixture is transferred to a vacuum oven and the tetrahydrothiophene-1,1-dioxide is removed at 180° C. (about 1 mm Hg). The solid is then added to a mechanically stirred solution of 15 g of water and 60 grams of acetone. The pH is adjusted to 5.5, and the resulting mixture is warmed to 45° C. The solution is stirred and cooled to 25° C. over a period of 1 h. The mixture is filtered to obtain a solid. The solid is washed 3 times with 30 grams of acetone and dried under vacuum to give the sodium salt of 4-sulfophenyl-7-[(1-oxyoctyl-1-methyl)amino] heptanoate. Data on the starting material and product prior to and after purification is summarized in Table I, entry 10.

Examples 11–12

Preparation of Sodium Salt of 4-sulfophenyl-6-[(1-oxy-2-methyloctyl)amino]hexanoate Step 1: Preparation of sodium salt of 4-sulfophenyl-6-[(1 -oxy-2-methyloctyl)amino]hexanoyl chloride: A 1 L 3-necked round-bottomed flask equipped with an overhead stirrer (mechanical), addition funnel, argon source, and cooling bath is charged with 27.1 g (0.100 mol) of 4-sulfophenyl-6-[(1-oxy-2-methyloctyl)amino]hexanoic acid (see Table I for metal content and purity of starting material) and 150 mL of diethyl ether. With stirring, 35.7 g (21.9 mL, 0.300 mol) of thionyl chloride is added in portions over a 5 min period. The resulting solution is stirred at room temperature for 10 min, and the ether and excess thionyl chloride are removed under vacuum and the oil is used for the next step without further purification. The preparation is represented by the following reaction:

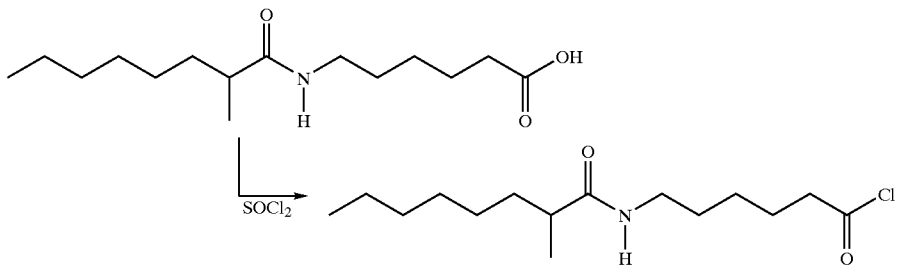

Step 2: Preparation of sodium salt of 4-sulfophenyl-6-[(1-oxy-2-methyloctyl)amino]hexanoate: A dry 500 mL 3-necked round-bottomed flask equipped with an overhead stirrer (mechanical), pH electrode, addition funnel, argon source, and cooling bath is charged with 39.2 g (0.200 mol) of the sodium salt of p-phenol sulfonate and 200 mL of 1.0 N sodium hydroxide solution. The resulting solution has a pH of 12.2. The solution is cooled in an ice bath and, with stirring, a solution of 4-sulfophenyl-6-[(1-oxy-2-methyloctyl)amino]hexanoyl chloride (prepared as described in Burns et al U.S. Pat. No. 5,523,434) in 100 mL of diethyl ether is added dropwise over a 10 minute period. The pH of the solution drops rapidly as the acid chloride solution is added. When the pH drops below 9.0 a 50% solution of sodium hydroxide is added dropwise to maintain the pH above 9.0. Upon addition of the acid chloride the reaction mixture becomes thick with suspended solid. Following completion of addition of the acid chloride the reaction mixture is stirred in the cold for 10 minutes. At this point the reaction mixture is thick with suspended solid and the pH has stabilized at 9.2. The ice bath is removed and the suspended solid is collected by filtration. This solid is dried under vacuum and transferred to a mechanically stirred solution of 90 grams of water and 360 grams of isopropyl alcohol. The pH is adjusted to 5.5, and the resulting mixture is warmed to 80° C. The solution is stirred and cooled to 25° C. over a period of 1–2 hours. The mixture is filtered to obtain a solid. The solid is washed 3 times with 180 grams of isopropyl alcohol and dried under vacuum to give the sodium salt of 4-sulfophenyl-6-[(1-oxy-2-methyloctyl) amino]hexanoate. Data on the starting material (acid) and product prior to and after purification is summarized in Table I, entry 9–10. The preparation is represented by the following reaction:

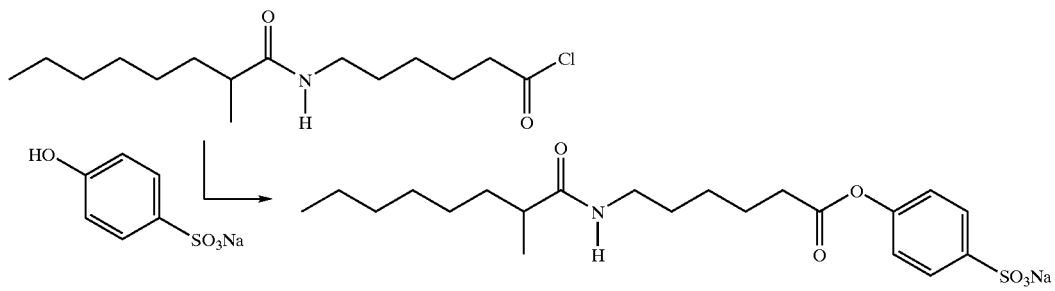

Note: recrystallization removes amine and lactam impurities. Remaining impurity include nonanoic acid and/or higher oligomers.

| Eg | Metal/conc (ppm) | Purity of C9AA | amine or lactam >0.1%? | Purity: crude product | % T of crude product | Equiv water used | Purity: purified product | Product Recovery | % T of purified product |
|---|---|---|---|---|---|---|---|---|---|
| 1 | Fe/<0.2 | 98.07 | No | 93.7 | 99 | 0 | 95.2 | 99% | 100 |
| 2 | Fe/0.5 | 98.07 | No | 91.1 | 95 | 0.3 | 98.6 | 99% | 100 |
| 3 | Fe/2 | 98.07 | No | 92.3 | 88 | 0.8 | 98.2 | 96% | 100 |
| 4 | Fe/10 | 98.07 | No | 89.5 | 70 | 1 | 98.8 | 92% | 99 |
| 5 | Fe/30 | 98.07 | No | 89.8 | 40 | 12 | 95.1 | 88% | 75 |
| 6 | Fe/<0.5 | 98.07 | Yes | 90.2 | 65 | 1 | 96.2 | 90% | 100 |
| 7 | Fe/<0.5 | 86.91 | Yes | 72.9 | 71 | 1 | 97.4 | 81% | 98 |
| 8 | Ni/10 | 92.46 | Yes | 88.0 | 79 | 1 | 96.4 | 90% | 100 |
| 9 | Ni/10 air | 92.46 | Yes | 88.6 | 69 | 1 | 98.8 | 89% | 97 |
| 10 | Ni/10 heat dry | 92.46 | Yes | 86.6 | 52 | 1 | 95.8 | 87% | 81 |
| 11 | Fe/<0.5 | 98.07 | No | 82.2 | 99 | 1 | 96.9 | 94% | 100 |
| 12 | Fe/>30 | 86.91 | Yes | 75.9 | 81 | 1 | 93 | 89% | 98 |

Note 1:
Aminoalkanoic acid or cyclic lactam present as impurity in >0.1 wt %
Total equivalents of water used as compared to product in purification procedure (ratio of water to product).
% T is measured at 370 nm on a methanolic solution of the product sample. Note: % T of 99 is unacceptable from a commericialization point of view.
Purity of crude product is based on the solvent free solid which is obtained by removing solvent via vacuum at a low enough temperature so as not to cause change in assay or color.

Bleach Additive and Detergent Compositions

The present invention also relates to bleaching additive and detergent compositions containing the bleach activators as produced by the novel processes described herein. These compositions would comprises the bleach activator and either a conventional bleach additive or a conventional detergent additive. The amount of bleach additive present in the bleaching additive composition is from about 0.1% to about 99.9%, preferably about 1% to about 95%, more preferably about 1% to about 80%. The amount of bleach activator present in the bleaching additive composition is from about 0.1% to about 99.9%, preferably about 0.1% to about 60%, more preferably about 0.1% to about 40%, even more preferably, still, about 0.1% to about 30%. The amount of detergent additive present in the detergent composition is from about 0.1% to about 99.9%, preferably about 1% to about 95%, more preferably about 1% to about 80%. The amount of bleach activator present in the detergent composition is from about 0.1% to about 99.9%, preferably about 0.1% to about 60%, more preferably about 0.1% to about 40%, even more preferably, still, about 0.1% to about 30%.

The conventional bleach additive and the conventional detergent additive are any additive which are commonly used in bleaching additive and detergent compositions. These can be selected from, but not limited to, bleaches, surfactants, builders, enzymes and bleach catalysts. It would be readily apparent to one of ordinary skill in the art what additives are suitable for inclusion into the compositions. The list exemplified herein is by no means exhaustive and should be only taken as examples of some suitable additives. It will also be readily apparent to one of ordinary skill in the art to only use those additives which are compatible with the bleach activators and other components in the composition, for example, bleach.

Of course, one of ordinary skill in the art will recognize that the present invention is not limited to the specific examples herein described or the ingredients and steps contained therein, but rather, may be practiced according to the broader aspects of the disclosure.

Example 13

Bleaching compositions having the form of granular laundry detergents are exemplified by the following formulations.

| INGREDIENT | A % | B % | C % | D % | E % |
|---|---|---|---|---|---|
| Bleach Activator* | 5 | 5 | 3 | 3 | 8 |
| Bleach Booster** | 0.2 | 0.2 | 1.0 | 0 | 0 |
| Sodium Percarbonate | 0 | 0 | 19 | 21 | 0 |
| Sodium Perborate monohydrate | 21 | 0 | 0 | 0 | 20 |
| Sodium Perborate tetrahydrate | 12 | 21 | 0 | 0 | 0 |
| Tetraacetylethylenediamine | 0 | 0 | 0 | 1 | 0 |
| Nonanoyloxybenzenesulfonate | 0 | 0 | 3 | 0 | 0 |
| Linear alkylbenzenesulfonate | 7 | 11 | 19 | 12 | 8 |
| Alkyl ethoxylate (C45E7) | 4 | 0 | 3 | 4 | 6 |
| Sodium tripolyphosphate | 20 | 0 | 0 | 17 | 0 |
| Zeolite A | 0 | 20 | 7 | 0 | 21 |
| SKS-6 ® silicate (Hoechst) | 0 | 0 | 11 | 11 | 0 |
| Trisodium citrate | 5 | 5 | 2 | 3 | 3 |
| Acrylic Acid/Maleic Acid copolymer | 4 | 0 | 4 | 5 | 0 |
| Sodium polyacrylate | 0 | 3 | 0 | 0 | 3 |
| Diethylenetriamine penta-(methylene phosphonic acid) | 0.4 | 0 | 0.4 | 0 | 0 |
| DTPA | 0 | 0.4 | 0 | 0 | 0.4 |
| EDDS | 0 | 0 | 0 | 0.3 | 0 |
| Carboxymethylcellulose | 0.3 | 0 | 0 | 0.4 | 0 |
| Protease | 1.4 | 0.3 | 1.5 | 2.4 | 0.3 |
| Lipolase | 0.4 | 0 | 0 | 0.2 | 0 |
| Cellulase | 0.1 | 0 | 0 | 0.2 | 0 |
| Anionic soil release polymer | 0.3 | 0 | 0 | 0.4 | 0.5 |
| Dye transfer inhibiting polymer | 0 | 0 | 0.3 | 0.2 | 0 |
| Carbonate | 16 | 14 | 24 | 6 | 23 |
| Silicate | 3.0 | 0.6 | 12.5 | 0 | 0.6 |
| Sulfate, Water, Perfume, Colorants | to 100 | to 100 | to 100 | to 100 | to 100 |

*Bleach activator according to any of Examples 1–12
**Bleach booster as described in U.S. Pat. Nos. 5,576,282, 5,710,116 and 5,817,614.

Example 14

This Example illustrates bleaching compositions, more particularly, liquid bleach additive compositions in accordance with the invention.

| Ingredients | A wt % | B wt % | C wt % | D wt % |
|---|---|---|---|---|
| NEODOL 91-10[1] | 6 | 5 | 7 | 4 |
| NEODOL 45-7[1] | 6 | 5 | 5 | 8 |
| NEODOL 23-2[1] | 3 | 5 | 3 | 3 |
| DEQUEST 2060[2] | 0.5 | 0.5 | 1.0 | 1.0 |
| Bleach Activator[3] | 6 | 6 | 4 | 7 |
| Bleach Booster[4] | 1 | 0 | 0.5 | 0.2 |
| Citric Acid | 0.5 | 0.5 | 0.5 | 0.5 |
| NaOH | to pH 4 | to pH 4 | to pH 4 | to pH 4 |
| Hydrogen Peroxide | 7 | 3 | 2 | 7 |
| Water | Balance to 100% | Balance to 100% | Balance to 100% | Balance to 100% |

[1]Alkyl ethoxylate available from The Shell Oil Company.
[2]Commercially available from Monsanto Co.
[3]Bleach Activator according to any of Examples 1–12.
[4]Bleach booster as described in U.S. Pat. Nos. 5,576,282, 5,710,116 and 5,817,614.

The compositions are used as bleach boosting additive (to be used in ADDITION to a bleach OR non-bleach detergent such as TIDE®). The additive is used at 1000 ppm.

Example 15

This Example illustrates cleaning compositions having bleach additive form, more particularly, liquid bleach additive compositions without a hydrogen peroxide source in accordance with the invention.

| Ingredients | A wt % | B wt % | C wt % | D wt % |
|---|---|---|---|---|
| NEODOL 91-10[1] | 6 | 5 | 7 | 10 |
| NEODOL 45-7[1] | 6 | 5 | 5 | 0 |
| NEODOL 23-2[1] | 3 | 5 | 3 | 5 |
| DEQUEST 2060[2] | 0.5 | 0.5 | 1.0 | 1.0 |
| Bleach Activator[3] | 6 | 6 | 4 | 7 |
| Bleach Booster[4] | 1 | 0 | 0.5 | 0.2 |
| Citric Acid | 0.5 | 0.5 | 0.5 | 0.5 |
| NaOH | to pH 4 | to pH 4 | to pH 4 | to pH 4 |
| Water | Balance to 100% | Balance to 100% | Balance to 100% | Balance to 100% |

[1]Alkyl ethoxylate available from The Shell Oil Company.
[2]Commercially available from Monsanto Co.
[3]Bleach Activator according to any of Examples 1–12.
[4]Bleach booster as described in U.S. Pat. Nos. 5,576,282, 5,710,116 and 5,817,614.

The compositions are used as bleach boosting additive (to be used in ADDITION to a bleach detergent such as TIDE® WITH BLEACH). The additive is used at 1000 ppm.

Example 16

Bleaching compositions having the form of granular laundry detergents are exemplified by the following formulations.

| INGREDIENT | A % | B % | C % | D % | E % |
|---|---|---|---|---|---|
| Bleach Activator* | 5 | 5 | 3 | 3 | 8 |
| Bleach booster** | 0.2 | 0.5 | 1.0 | 0.7 | 0 |
| Sodium Percarbonate | 0 | 5 | 15 | 0 | 0 |
| Sodium Perborate monohydrate | 5 | 0 | 0 | 10 | 20 |
| Brightener 49 | 0.4 | 0.4 | 0 | 0 | 0 |
| NaOH | 2 | 2 | 2 | 0 | 2 |
| Linear alkylbenzenesulfonate, partially neutralized | 9 | 9 | 9 | 9 | 9 |
| Alkyl ethoxylate (C25E9) | 7 | 7 | 5 | 4 | 6 |
| Zeolite A | 32 | 20 | 7 | 17 | 21 |
| Acrylic Acid/Maleic Acid copolymer | 0 | 0 | 4 | 5 | 8 |
| Sodium polyacrylate | 0.6 | 0.6 | 0.6 | 0 | 0 |
| Diethylenetriamine penta-(methylene phosphonic acid) | 0.5 | 0 | 0.5 | 0 | 1 |
| EDDS | 0 | 0.5 | 0 | 0.5 | 0 |
| Protease | 1 | 1 | 1.5 | 2.4 | 0.3 |
| Lipolase | 0 | 0 | 0 | 0.2 | 0 |
| Cellulase | 0 | 0 | 0 | 0.2 | 0 |
| Anionic soil release polymer | 0 | 0 | 0.5 | 0.4 | 0.5 |
| Dye transfer inhibiting polymer | 0 | 0 | 0.3 | 0.2 | 0 |
| Soda Ash | 22 | 22 | 22 | 22 | 22 |
| Silicate (2r) | 7.0 | 7.0 | 7.0 | 7.0 | 7.0 |
| Sulfate, Water, Perfume, Colorants | to 100 | to 100 | to 100 | to 100 | to 100 |

*Bleach activator according to any of Examples 1–12.
**Bleach booster as described in U.S. Pat. Nos. 5,576,282, 5,710,116 and 5,817,614.

Any of the above compositions is used to launder fabrics under mildly alkaline conditions (pH 7–8). The pH can be adjusted by altering the proportion of acid to Na-salt form of alkylbenzenesulfonate.

Example 17

A granular automatic dishwashing detergent composition comprises the following.

| INGREDIENT | A wt % | B wt % | C wt % | D wt % |
|---|---|---|---|---|
| Bleach Activator (See Note 1) | 3 | 4.5 | 2.5 | 4.5 |
| Sodium Perborate Monohydrate (See Note 2) | 1.5 | 0 | 1.5 | 0 |
| Sodium Percarbonate (See Note 2) | 0 | 1.2 | 0 | 1.2 |
| Amylase (TERMAMYL ® from NOVO) | 1.5 | 2 | 2 | 2 |
| Dibenzoyl Peroxide | 0 | 0 | 0.8 | 0 |
| Transition Metal Bleach Catalyst (See Note 3) | 0 | 0.1 | 0.1 | 0 |
| Bleach Booster (See Note 4) | 0 | 0.2 | 0.55 | 0.2 |
| Protease (SAVINASE ® 12 T, NOVO, 3.6% active protein) | 2.5 | 2.5 | 2.5 | 2.5 |
| Trisodium Citrate Dihydrate (anhydrous basis) | 7 | 15 | 15 | 15 |
| Citric Acid | 14 | 0 | 0 | 0 |
| Sodium Bicarbonate | 15 | 0 | 0 | 0 |
| Sodium Carbonate, anhydrous | 20 | 20 | 20 | 20 |
| BRITESIL H2O ®, PQ Corp. (as $SiO_2$) | 7 | 8 | 7 | 5 |
| Diethylenetriaminepenta(methylenephosphonic acid), Na | 0 | 0 | 0 | 0.2 |
| Hydroxyethyldiphosphonate (HEDP), Sodium Salt | 0 | 0.5 | 0 | 0.5 |
| Ethylenediaminedisuccinate, Trisodium Salt | 0.1 | 0.3 | 0 | 0 |
| Dispersant Polymer (Accusol 480N) | 6 | 5 | 8 | 10 |
| Nonionic Surfactant (LF404, BASF) | 2.5 | 1.5 | 1.5 | 1.5 |
| Paraffin (Winog 70 ®) | 1 | 1 | 1 | 0 |
| Benzotriazole | 0.1 | 0.1 | 0.1 | 0 |
| Sodium Sulfate, water, minors BALANCE TO: | 100% | 100% | 100% | 100% |

Note 1: Bleach Activator according to any of Examples 1–12.
Note 2: These hydrogen peroxide sources are expressed on a weight % available oxygen basis. To convert to a basis of percentage of the total composition, divide by about 0.15.
Note 3: Transition Metal Bleach Catalyst: Pentamaineacetatocobalt (III) nitrate; may be replaced MnTACN.
Note 4: Bleach booster as described in U.S. Pat. Nos. 5,576,282, 5,710,116 and 5,817,614.

Example 18

A granular automatic dishwashing detergent composition comprising the following.

| INGREDIENT | A wt % | B wt % | C wt % | D wt % |
|---|---|---|---|---|
| Bleach Activator (See Note 1) | 3 | 4.5 | 2.5 | 4.5 |
| Sodium Perborate Monohydrate (See Note 2) | 1.5 | 0 | 1.5 | 0 |
| STPP (anhydrous) (See Note 4) | 31 | 26 | 45 | 50 |
| Sodium Percarbonate (See Note 2) | 0 | 1.5 | 0 | 1.5 |
| Amylase (See Note 5) | 1.5 | 1.5 | 1.62 | 1.62 |
| Transition Metal Bleach Catalyst (See Note 3) | 0 | 0 | 0.016 | 0.008 |
| Protease (See Note 6) | 2.2 | 1.26 | 0 | 1.5 |
| Bleach Booster (See Note 7) | 0 | 0.2 | 0.42 | 0.88 |
| Sodium Carbonate, anhydrous | 32 | 22 | 5 | 14 |
| BRITESIL H2O ®, PQ Corp. (as SiO$_2$) | 9 | 7 | 8 | 8 |
| Nonionic Surfactant (LF404, BASF) | 1 | 0.5 | 1.5 | 2 |
| Sodium Sulfate, water, minors BALANCE TO: | 100% | 100% | 100% | 100% |

Note 1: Bleach Activator according to any of Examples 1–12.
Note 2: These hydrogen peroxide sources are expressed on a weight % available oxygen basis. To convert to a basis of percentage of the total composition, divide by about 0.15.
Note 3: Transition Metal Bleach Catalyst: Pentamaineacetato-cobalt (III) nitrate; may be replaced MnTACN.
Note 4: Sodium tripolyphosphate.
Note 5: The amylase is selected from: Termamyl ®, Fungamyl ®; Duramyl ®; BAN ®, and the amylases as described in WO95/26397 and in co-pending application by Novo Nordisk PCT/DK/96/00056.
Note 6: The protease is selected from: Savinase ®; Maxatase ®; Maxacal ®; Maxapem 15 ®; subtilisin BPN and BPN'; Protease B; Protease A; Protease C, Protease D; Primase ®; Durazym ®; Opticlean ®; and Optimase ®; and Alcalase ®.
Note 7: Bleach booster as described in U.S. Pat. Nos. 5,576,282, 5,710,116 and 5,817,614.

What is claimed is:

1. A process for preparing a 4-sulfophenyl-[(1-oxyalkanoyl)amino]alkanoate comprising the steps of:

reacting an acetoxy benzene sulfonate salt with a high purity amido carboxylic acid, wherein said high purity amido carboxylic acid comprises least about 90% by weight, of an amido carboxylic acid of the formula:

wherein R is $C_5$–$C_{21}$ hydrocarbyl, $R^1$ is selected from hydrogen and $C_1$–$C_3$ alkyl, and n is an integer from about 1 to about 8; and less than about 10% by weight, of color forming bodies;
wherein said process is performed in the presence of less than 10 ppm of transition metal.

2. A process according to claim 1, wherein said high purity amido carboxylic acid comprises least about 95% by weight, of a amido carboxylic acid of the formula:

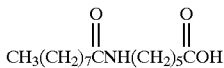

3. A process according to claim 1, wherein said high purity amido carboxylic acid is produced by the reaction of a carboxylic acid of the formula:

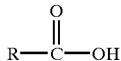

wherein R is $C_5$–$C_{21}$ hydrocarbyl; with a lactam of the formula:

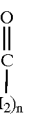

wherein $R^1$ is selected from hydrogen and $C_1$–$C_3$ alkyl, and n is an integer from 1 to 8.

4. A process according to claim 1, wherein said process is further conducted in the presence of at least about 0.1 mole equivalent of a tertiary amine.

5. A process according to claim 1, wherein said process is further conducted in the presence of terahydrothiophene-1,1-dioxide.

6. A process according to claim 1, wherein said process is further conducted in the presence of about 0.1 mole equivalent of sodium acetate.

7. A process according to claim 1, wherein said process for preparing a purified salt of 4-sulfophenyl-[(1-oxyalkanoyl)amino]alkanoate comprises the steps of:

(a) reacting an alkali metal salt of 4-hydroxybenzene sulfonic acid with a $C_2$ to $C_4$ carboxylic anhydride at a sufficient temperature and time in a reaction solvent to form a reaction mixture having an alkali metal salt of 4-acyloxybenzenesulfonic acid and a $C_2$ to $C_4$ carboxylic acid, wherein the alkali metal salt of 4 hydroxybenezene sulfonic acid and $C_2$ to $C_4$ carboxylic anhydride are present in a mole ratio of 1:1 to 1:40, respectively, and the reaction solvent is present in a weight ratio of 1:1 to 20:1 based on the weight of the alkali metal salt of 4-hydroxybenzene sulfonic acid, provided that excess carboxylic anhydride is removed under reduced pressure from the reaction vessel;

(b) adding a [(1-oxyalkanoyl)amino]alkanoic acid and at least one transesterification catalyst to said reaction mixture and heating at a temperature of from about 120° C. to about 220° C. for from about 0.5 to about 10 hours and a pressure sufficient to maintain reflux of said reaction solvent and to remove the $C_2$ to $C_4$ carboxylic acid from the reaction vessel, to form a reaction product containing a salt of 4-sulfophenyl-[(1-oxyalkanoyl) amino]alkanoate wherein the moles of the [(1-oxyalkanoyl)amino]alkanoic acid added is 0.7 to 5 times the moles of the alkali metal salt of 4-hydroxybenzene sulfonic acid;

(c) admixing said reaction product including reaction solvent and a salt of 4-sulfophenyl-[(1-oxyalkanoyl) amino]alkanoate with a water-based purification system to form a purification mixture, said water-based purification system including a processing aid and having water present at a ratio of 4-sulfophenyl-[(1- oxyalkanoyl)amino]alkanoate to water ranging from about 1:0.05 to about 1:50;

(d) separating a purified salt of 4-sulfophenyl-[(1-oxyalkanoyl)amino]alkanoate from said purification mixture; and (e) collecting said purified salt of 4-sulfophenyl-[(1-oxyalkanoyl)amino]alkanoate.

8. 4-sulfophenyl-[(1-oxyalkanoyl)amino]alkanoate prepared according to the process of claim 1.

9. A cleaning composition containing 4-sulfophenyl-[(1-oxyalkanoyl)amino]alkanoate prepared according to the process of claim 1.

* * * * *